US010806863B2

(12) United States Patent
Yamada et al.

(10) Patent No.: US 10,806,863 B2
(45) Date of Patent: Oct. 20, 2020

(54) NEEDLELESS SYRINGE

(71) Applicant: DAICEL CORPORATION, Osaka (JP)

(72) Inventors: Ryohei Yamada, Prachinburi (TH); Tomohide Fujiwara, Hyogo (JP); Yuzo Yamamoto, Hyogo (JP)

(73) Assignee: Daicel Corporation, Osaka (JP)

( * ) Notice: Subject to any disclaimer, the term of this patent is extended or adjusted under 35 U.S.C. 154(b) by 360 days.

(21) Appl. No.: 15/507,726

(22) PCT Filed: Aug. 18, 2015

(86) PCT No.: PCT/JP2015/073069
§ 371 (c)(1),
(2) Date: Feb. 28, 2017

(87) PCT Pub. No.: WO2016/031613
PCT Pub. Date: Mar. 3, 2016

(65) Prior Publication Data
US 2017/0304544 A1 Oct. 26, 2017

(30) Foreign Application Priority Data
Aug. 29, 2014 (JP) .................. 2014-175925

(51) Int. Cl.
*A61M 5/30* (2006.01)
*A61M 5/20* (2006.01)

(52) U.S. Cl.
CPC ......... *A61M 5/3007* (2013.01); *A61M 5/2053* (2013.01); *A61M 2205/8206* (2013.01); *A61M 2205/8231* (2013.01)

(58) Field of Classification Search
CPC .............. A61M 4/3007; A61M 5/2053; A61M 2205/8206; A61M 2205/8231
See application file for complete search history.

(56) References Cited

U.S. PATENT DOCUMENTS 2,653,602 A * 9/1953 Smoot ..................... A61M 5/30
60/716
4,124,024 A * 11/1978 Schwebel ............... A61M 5/30
604/130
(Continued)

FOREIGN PATENT DOCUMENTS

CN 103209725 A 7/2013
EP 0888791 A1 1/1999
(Continued)

OTHER PUBLICATIONS

Office Action dated Oct. 31, 2017 in related Japanese Application No. 2014-175925.
(Continued)

*Primary Examiner* — Lauren P Farrar
(74) *Attorney, Agent, or Firm* — Knobbe Martens Olson & Bear LLP

(57) ABSTRACT

A needleless syringe comprises a main syringe body which is a main body thereof and which has, in the main body, a sliding movement passage connected to an opening provided on a front end surface of the main body; a holding unit which has an accommodating unit for accommodating an injection objective substance so that the injection objective substance is releasable; and a driver that is configured to apply energy to the holding unit in order to allow the holding unit to slide toward the opening. When the energy is applied by the driver to the holding unit disposed at the initial position, the holding unit slides in the sliding movement passage to abut against the opening at the abutment position, and thus the injection objective substance accommodated in the accommodating unit is discharged via the opening. Accordingly, the high injection performance of the needleless syringe is appropriately exhibited.

19 Claims, 5 Drawing Sheets

(56) References Cited

U.S. PATENT DOCUMENTS

| | | | |
|---|---|---|---|
| 4,945,050 A | 7/1990 | Sanford et al. | |
| 5,371,015 A * | 12/1994 | Sanford | C12M 35/04 |
| | | | 435/285.3 |
| 6,475,181 B1 | 11/2002 | Potter et al. | |
| 6,913,593 B1 | 7/2005 | Alexandre et al. | |
| 6,979,310 B2 * | 12/2005 | Navelier | A61M 5/30 |
| | | | 604/68 |
| 7,182,748 B1 | 2/2007 | Potter et al. | |
| 8,133,494 B2 | 3/2012 | zur Megede et al. | |
| 2002/0058907 A1 | 5/2002 | Deboer et al. | |
| 2002/0091353 A1 * | 7/2002 | Bellhouse | A61M 5/3015 |
| | | | 604/68 |
| 2002/0183689 A1 | 12/2002 | Alexandre et al. | |
| 2004/0049151 A1 | 3/2004 | Lell | |
| 2004/0215135 A1 | 10/2004 | Sheldrake et al. | |
| 2006/0281175 A1 | 12/2006 | Mcswiggen et al. | |
| 2008/0132450 A1 | 6/2008 | Lee et al. | |
| 2010/0040619 A1 | 2/2010 | Li et al. | |
| 2014/0200512 A1 | 7/2014 | Oda | |

FOREIGN PATENT DOCUMENTS

| | | |
|---|---|---|
| GB | 680743 A | 10/1952 |
| JP | 2002-507920 A | 3/2002 |
| JP | 2002-507921 A | 3/2002 |
| JP | 2002-521148 A | 7/2002 |
| JP | 2002-538901 A | 11/2002 |
| JP | 2003-520073 A | 7/2003 |
| JP | 2004-500933 A | 1/2004 |
| JP | 2004-521677 A | 7/2004 |
| JP | 2005-523679 A | 8/2005 |
| JP | 2007-525192 A | 9/2007 |
| JP | 2008-508881 A | 3/2008 |
| JP | 2008-206477 A | 9/2008 |
| JP | 2010-503616 A | 2/2010 |
| JP | 2014-104112 A | 6/2014 |
| JP | 2014-104113 A | 6/2014 |
| WO | WO 02/07803 A1 | 1/2002 |

OTHER PUBLICATIONS

The International Search Report issued in corresponding application PCT/JP2015/073069 dated Oct. 20, 2015.

International Preliminary Report on Patentability issued for related application PCT/JP2015/073069 dated Mar. 9, 2017.

Notification of Cancellation of Reconsideration by Examiner Before Appeal dated Sep. 11, 2018 in corresponding Japanese Application No. 2014-175925.

Final Decision of Rejection dated Mar. 13, 2018 in related Japanese Application No. 2014-175925.

Extended European Search Report dated May 4, 2018 in related European Application No. 15836796.1.

* cited by examiner

NEEDLELESS SYRINGE

This application is a U.S. national phase application of PCT/JP2015/073069 filed on Aug. 18, 2015 that claims the benefit of Japanese Patent Application No. 2014-175925, filed Aug. 29, 2014, each of which is incorporated by reference herein in its entirety.

TECHNICAL FIELD

The present invention relates to a needleless syringe for injecting an injection objective substance into an injection target area without using any injection needle.

BACKGROUND ART

A needleless syringe is widely known, in which an injection solution is discharged without using any injection needle to perform the injection into a target. For example, Patent Literature 1 discloses a needleless syringe in which a medicament is injected by utilizing a pressurized gas. In particular, the needleless syringe includes a destroying unit which makes sliding movement in accordance with an operation performed by a user, while accommodating a cartridge filled with the pressurized gas, wherein a granular drug capsule, which is held or retained by a cylindrical holding unit, is arranged at a forward end portion thereof. The drug capsule has a flange, and the drug capsule is held by interposing the flange between a piston and a holding member. The following fact is disclosed. That is, when the forward end of the cartridge is destroyed in accordance with the sliding movement of the destroying unit, then the piston flies by means of the pressurized gas coming from the cartridge, and the piston abuts against a shoulder portion. In this situation, the pressure is raised at the back of the drug capsule. The drug capsule is broken, the drug is allowed to flow by the pressurized gas, and the drug is administered to the skin.

PRIOR ART LITERATURE

Patent Literature

Patent Literature 1: U.S. Pat. No. 6,475,181

SUMMARY OF THE INVENTION

Problems to be Solved by the Invention

When the injection is performed, for example, with respect to the skin of a living body while allowing the medicament such as a powder to ride on the flow of the pressurized gas as performed in the conventional technique, a variety of difficult situations may practically arise. When the medicament is carried to the skin by the flow of the pressurized gas, the medicament is easily converted into fine particles by the energy received from the pressurized gas. On this account, the masses of the respective medicament particles become light. As a result, the momentums, which are possessed by the respective particles, are lowered. Thus, it becomes difficult to allow the medicament to penetrate through the skin or the like by means of the pressurized gas, which results in the deterioration of the medicament injection performance to be brought about by the needleless syringe.

Further, it is feared that the medicament, which is converted into the fine particles by the pressurized gas, may be diffused, the medicament may be pressed and adhered under pressure to the inner wall surface of the flow passage such as a nozzle or the like (flow passage in which the medicament flows together with the pressurized gas), and the amount of the medicament discharged from the needleless syringe may be decreased. As a result, the ability to discharge the medicament, which is brought about by the needleless syringe, may be dispersed, and the medicament tends to be worthlessly used. Further, in the case of the conventional technique, the high pressure gas is allowed to blow against the medicament to be injected, and the medicament is allowed to abut against the skin together with the gas. When the high pressure gas is allowed to directly blow against the medicament to be injected as described above, it is difficult to appropriately transmit the energy possessed by the high pressure gas to the medicament. It is difficult to sufficiently accelerate the medicament. Also from the viewpoint as described above, in the case of the conventional technique, it is still difficult to apply, to the medicament, the momentum required to penetrate through the skin or the like. Thus, it is impossible to obtain any sufficient medicament injection performance to be brought about by the needleless syringe.

Accordingly, in view of the problems described above, an object of the present invention is to appropriately exhibit the high injection performance of such a needleless syringe that an injection objective substance, which is a medicament or the like to be injected into a living body, is injected into an injection target area of the living body.

Means for Solving the Problems

In order to solve the problems described above, the present invention adopts the following construction in a needleless syringe for injecting an injection objective substance (for example, a medicament or the like) without using any injection needle. That is, the energy for the injection is not directly applied to the injection objective substance, but a holding unit, which accommodates the injection objective substance, is driven by the energy applied from the outside, and the holding unit is allowed to abut against a main syringe body, and the momentum, which has been possessed by the holding unit, is transferred to the injection objective substance. Thus, the discharge of the injection objective substance is performed effectively.

Specifically, the present invention resides in a needleless syringe for injecting an injection objective substance into an injection target area of a living body without using any injection needle; the needleless syringe comprising a main syringe body which is a main body of the needleless syringe and which has, in the main body, a sliding movement passage connected to an opening provided on a front end surface of the main body; a holding unit which is arranged slidably in the sliding movement passage and which has an accommodating unit for accommodating the injection objective substance so that the injection objective substance is releasable; and a driver that is configured to apply energy to the holding unit arranged at an initial position separated by a predetermined distance from the opening in the sliding movement passage in order to allow the holding unit to slide toward the opening. Further, in the needleless syringe, the opening is arranged so that the opening adjoins the accommodating unit when the holding unit is at an abutment position at which the holding unit abuts against the opening and sliding movement thereof is inhibited in the sliding movement passage. In this situation, the accommodating unit is formed at an end surface of the holding unit facing the opening so that the accommodating unit does not penetrate in an axial direction of the holding unit. The term "axial direction" referred to in this specification refers to the direction in which the holding unit slides along the sliding movement passage. Further, when the energy is applied by the driver to the holding unit disposed at the initial position, then the holding unit slides in the sliding movement passage to abut against the opening at the abutment position, and thus the injection objective substance accommodated in the accommodating unit is discharged via the opening.

In the needleless syringe according to the present invention, a variety of known energy generating modes can be adopted as the energy source of the driver, provided that the energy can be transmitted to the holding unit which is disposed at the initial position in the sliding movement passage. For example, it is possible to adopt an ignition charge to be ignited by an igniter and a gas producing agent to produce the gas by means of the combustion. Further, as for the mode of the driver other than the above, the release of the energy of an elastic member such as a spring or the like or the energy of a compressed gas may be utilized as the energy to be applied to the holding unit. Alternatively, it is also allowable to utilize, for example, a solenoid actuator or an electromagnetic valve driven by the voltage application from a power source circuit. Further alternatively, a piston, which is fixed by an urging spring, may be released by the driving source as described above, and the accumulated elastic energy of the urging spring may be utilized as the energy to be applied to the holding unit. The energy of the driver as described above is applied to the holding unit directly or indirectly. In the present invention, any hole, which penetrates in the axial direction, is not formed for the holding unit. The injection objective substance is in a state of being held or retained by the holding unit. For example, the accommodating unit may be a depression or recess formed on the holding unit facing or confronting the side of the opening. Therefore, even when the holding unit is suddenly moved in the axial direction during the operation, the whole quantity of the injection objective substance is extruded toward the opening. Accordingly, it is possible to exclude the remaining in the syringe as far as possible. Further, when the holding unit is driven by the gas, the whole quantity of the energy, which is brought about by the produced gas, also abuts against the holding unit directly or indirectly. It is possible to effectively drive the holding unit.

Note that when the combustion energy of the ignition charge is utilized, the ignition charge may be, for example, any one of propellants of a propellant containing zirconium and potassium perchlorate, a propellant containing titanium hydride and potassium perchlorate, a propellant containing titanium and potassium perchlorate, a propellant containing aluminum and potassium perchlorate, a propellant containing aluminum and bismuth oxide, a propellant containing aluminum and molybdenum oxide, a propellant containing aluminum and copper oxide, and a propellant containing aluminum and iron oxide, or a propellant composed of a combination of a plurality of the foregoing propellants. Further, when the energy generated by the gas producing agent is utilized, it is also possible to use, as the gas producing agent, a single base smokeless propellant and a variety of gas producing agents used for a gas generator for an air bag and a gas generator for a seat belt pretensioner.

The holding unit, to which the energy is applied from the driver, is arranged so that the holding unit is slidable in the sliding movement passage which is formed at the inside of the main syringe body. Therefore, the applied energy is used as the energy for propelling and sliding the holding unit in the sliding movement passage. Then, the holding unit is provided with the accommodating unit. The injection objective substance is accommodated in the accommodating unit so that the injection objective substance is releasable. Therefore, when the holding unit is allowed to slide by applying the energy, the injection objective substance, which is accommodated in the accommodating unit, is also propelled in the sliding movement passage together with the holding unit. Note that in this specification, the term "releasable" does not mean the fact that the accommodation state in the accommodating unit is always maintained but means the fact that the accommodation state disappears on account of any reason to provide a state in which the substance may be released from the accommodating unit.

In this case, the opening is provided at the end portion of the sliding movement passage, i.e., on the side of the front end surface of the main syringe body. The opening defines the space which connects the sliding movement passage and the space disposed outside of the main syringe body. Further, in this specification, the term "front" refers to the direction in which the injection objective substance is discharged from the needleless syringe. Therefore, the opening connects the sliding movement passage in which the holding unit exists and the exterior space in which the injection target area of the living body exists, in order that the injection objective substance, which is accommodated by the accommodating unit of the holding unit, is discharged frontwardly. The opening, which is connected to the sliding movement passage like this, is constructed to abut against the holding unit and inhibit the sliding movement thereof when the holding unit slides along the sliding movement passage. Note that the position, at which the sliding holding unit abuts against the opening, is referred to as "abutment position". Therefore, the holding unit slides from the initial position to the abutment position in the sliding movement passage by means of the energy applied from the driver.

In this case, the relative arrangement and the positional relationship between the opening and the holding unit are determined in order that the opening adjoins the accommodating unit of the holding unit when the holding unit is disposed at the abutment position in the sliding movement passage. Further, the injection objective substance is in a state of being accommodated in the accommodating unit on the holding unit in a state which is provided before the discharge of the injection objective substance is performed by the needleless syringe, i.e., in a state in which the holding unit is positioned at the initial position. Then, when the energy is applied by the driver, the injection objective substance progressively slides toward the opening along the sliding movement passage together with the holding unit in the state in which the injection objective substance is releasably accommodated. After that, when the holding unit arrives at the abutment position, the sliding movement of the holding unit is inhibited by the abutment between the holding unit and the opening. On the other hand, the momentum, which has been possessed by the holding unit including the injection objective substance, is transferred to the injection objective substance having been releasably accommodated in the accommodating unit. In accordance with the momentum, the injection objective substance is separated from the holding unit, and the injection objective substance is released toward the opening. Then, the injection objective substance, which is released toward the opening, passes through the space which is defined by the opening as described above, and the injection objective substance is discharged to the injection target area of the living body positioned at the outside of the main syringe body. The injection of the injection objective substance into the area is realized.

According to the needleless syringe having the structure for discharging the injection objective substance as described above, the energy, which is applied from the driver, is converted into the discharge energy of the injection objective substance by the aid of the sliding movement of the holding unit, and the injection objective substance is discharged to the injection target area. That is, the needleless syringe has such a structure that the energy applied from the driver is not directly the discharge energy for the injection objective substance. Therefore, it is possible to avoid an inconvenience which would be otherwise caused by the formation of fine particles of the injection objective substance by the energy applied from the driver. Further, the holding unit exists physically in the sliding movement passage. Therefore, it is possible to suppress such a situation that the medium (for example, the combustion gas or the high pressure gas) of the energy applied from the driver is brought in contact with the injection objective substance or the medium is mixed with the injection objective substance. It is affirmed that this feature is preferred in view of the hygiene in order to inject the injection objective substance into the injection target area of the living body. In this manner, according to the needleless syringe concerning the present invention, the high injection performance for injecting the injection objective substance is appropriately exhibited.

Note that in the needleless syringe according to the present invention, the injection objective substance includes a component for which the efficacy is expected at the objective portion of the injection target area. Therefore, any accommodating state of the injection objective substance in the accommodating unit is available without causing any problem, and any specified physical form of the injection objective substance is available without causing any problem, including, for example, liquid, fluid, for example, in a gel form, powder, solid, for example, in a granular form, provided that at least the discharge can be performed in accordance with the discharge construction described above. For example, the injection objective substance is a liquid. Even when the injection objective substance is a solid, it is also allowable to use a solid in a gel form or a powder which makes it possible to perform the discharge. Further, the component, which is to be fed into the objective portion of the injection target area, is contained in the injection objective substance. The component may exist in such a state that the component is dissolved in the injection objective substance, or the component may be in such a state that the component is simply mixed without being dissolved. For example, the component to be fed includes, for example, vaccine for enhancing antibody, protein for beauty, and cultured cells for regenerating hair. The injection objective substance is formed by containing the component in a liquid or a fluid in a gel form or the like so that the component as described above can be discharged. Alternatively, it is also allowable that the injection objective substance is not a predetermined substance itself. The injection objective substance may be an inclusion such as a capsule or the like in which the predetermined substance is included. Further, it is also allowable that the injection objective substance is not a medicament or the like which exhibits the medical effect in the injection target area. The injection objective substance may be buried or embedded in the living body for any predetermined purpose. For example, a minute IC chip or the like, in which an identification number of a living body or the like is recorded, may be used as the injection objective substance.

In this context, as for the needleless syringe described above, a space on a driver side on which the driver is arranged and a space on an opening side which is connected to the opening may be formed to be hermetically isolated from each other by the holding unit in the sliding movement passage. When the space on the driver side and the space on the opening side are hermetically isolated from each other while interposing the holding unit as described above, it is thereby possible to maximally suppress such an opportunity that the medium (for example, the combustion gas and the high pressure gas as described above), which relates to the application of the energy to the holding unit, is brought in contact with the injection objective substance which is accommodated in the accommodating unit. It is possible to form an injection environment which is preferred in view of the hygiene.

Further, in the needleless syringe described above, when the driver is an ignition device in which a propellant is combusted by supplying an electric power from outside, the accommodating unit may be formed to be arranged at the end surface disposed on a side opposite to an end surface of the holding unit with which a combustion product of the propellant is brought in contact. When the needleless syringe is constructed as described above, the combustion product, which is produced in accordance with the combustion of the propellant, is blocked or shut off by the holding unit. Therefore, it is possible to reliably exclude such an opportunity that the combustion product is brought in contact with the injection objective substance accommodated in the accommodating unit. It is possible to realize the more hygienic injection.

In this context, in the needleless syringe described above, the accommodating units may be arranged at a plurality of positions on the end surface of the holding unit disposed on a side of the opening when the holding unit is disposed at the abutment position in the sliding movement passage. The injection objective substance is arranged at the plurality of positions of the holding unit, and thus the injection objective substance is discharged in a wide area with respect to the injection target area. Therefore, it is possible to realize the preferred injection.

Further, in the needleless syringe described above, an inner diameter of the opening may be formed to be smaller than an inner diameter of the sliding movement passage. Then, an end surface area of the accommodating unit disposed on a side of the opening is formed to be overlapped so that the end surface area is included in an opening area of the opening when the holding unit is disposed at the abutment position. The correlation between the inner diameter of the sliding movement passage and the inner diameter of the opening, and the correlation between the opening area of the opening and the end surface area of the accommodating unit are set as described above. Accordingly, when the injection objective substance is released from the accommodating unit in accordance with the abutment of the holding unit against the opening at the abutment position, the injection objective substance can smoothly pass through the opening to arrive at the injection target area. It is affirmed that this feature is extremely useful in view of the efficient utilization of the injection objective substance.

Then, more specifically, in the needleless syringe described above, the main syringe body may have a predetermined thickness in a discharge direction of the injection objective substance at the front end surface at which the opening is provided, and thus a flying space, in which the injection objective substance flies, may be formed in the opening. The flying space, which is provided for allowing the injection objective substance released from the accommodating unit to fly, is secured by the front end surface of the main syringe body having the predetermined thickness as described above. Accordingly, when the holding unit abuts against the opening at the abutment position, the momentum, which has been possessed by the holding unit, can be efficiently transferred to the injection objective substance. It is possible to improve the injection performance of the needleless syringe.

Further, in place of the mode in which the flying space is formed as described above, the needleless syringe described above may further comprise a spacer which is formed to surround the opening at outside of the front end surface of the main syringe body and which protrudes frontwardly from the main syringe body. Then, in this case, a communication passage, which makes communication between an internal space of the spacer and an external space of the spacer in a state of abutment of the spacer against the injection target area, is provided for the spacer. When the spacer is provided as described above, it is also thereby possible to form the space for allowing the injection objective substance to fly in the same manner as the flying space described above, depending on the height of protrusion of the spacer. Further, when the holding unit slides in the sliding movement passage, the air, which has been present in the sliding movement passage before the discharge of the injection objective substance, is extruded to the outside of the syringe. Accordingly, the communication passage is provided for the spacer, and the excluded air is discharged to the external space of the spacer. Thus, it is possible to mitigate the resistance of the air against the released injection objective substance, and it is possible for the injection objective substance to appropriately arrive at the injection target area.

In this context, the needleless syringe described above may further comprise a rod to which the energy applied from the driver is applied prior to the holding unit, and a rod movement passage which is provided in nonparallel to the sliding movement passage in the main syringe body and which allows the rod to move therein. Then, the holding unit is arranged at the initial position so that a tail portion, which is disposed on a side opposite in the axial direction to a side of formation of the accommodating unit, protrudes into the rod movement passage. In this case, when the energy is applied to the rod by the driver, then the rod moves in the rod movement passage, the rod is brought in contact with the holding unit disposed at the initial position, and thus the sliding movement of the holding unit is started in the sliding movement passage. In the case of the needleless syringe constructed as described above, the rod firstly receives the application of the energy from the driver, and the rod moves in the rod movement passage. After that, the rod is brought in contact with the holding unit to transmit the energy thereof. Thus, the sliding movement of the holding unit is started in the sliding movement passage. Then, the rod movement passage in which the rod moves and the sliding movement passage are formed in nonparallel to one another in the main syringe body. Accordingly, in relation to the needleless syringe, it is easy to select the arrangement of the driver which applies the energy with respect to the sliding movement of the holding unit in the sliding movement passage. For example, it is possible to improve the degree of freedom of the design of the needleless syringe, and it is possible to realize the compact needleless syringe.

Advantageous Effect of the Invention

It is possible to appropriately exhibit the high injection performance of such a needleless syringe that the injection objective substance, which is the medicament or the like to be injected into the living body, is injected into the injection target area of the living body.

EMBODIMENTS FOR CARRYING OUT THE INVENTION

An explanation will be made below with reference to the drawings about a needleless syringe 1 (hereinafter simply referred to as "syringe 1") according to an embodiment of the present invention. Note that the following structure or construction of the embodiment is described by way of example. The present invention is not limited to the structure or construction of the embodiment.

First Embodiment

<Structure of Syringe 1>

Figure 1:
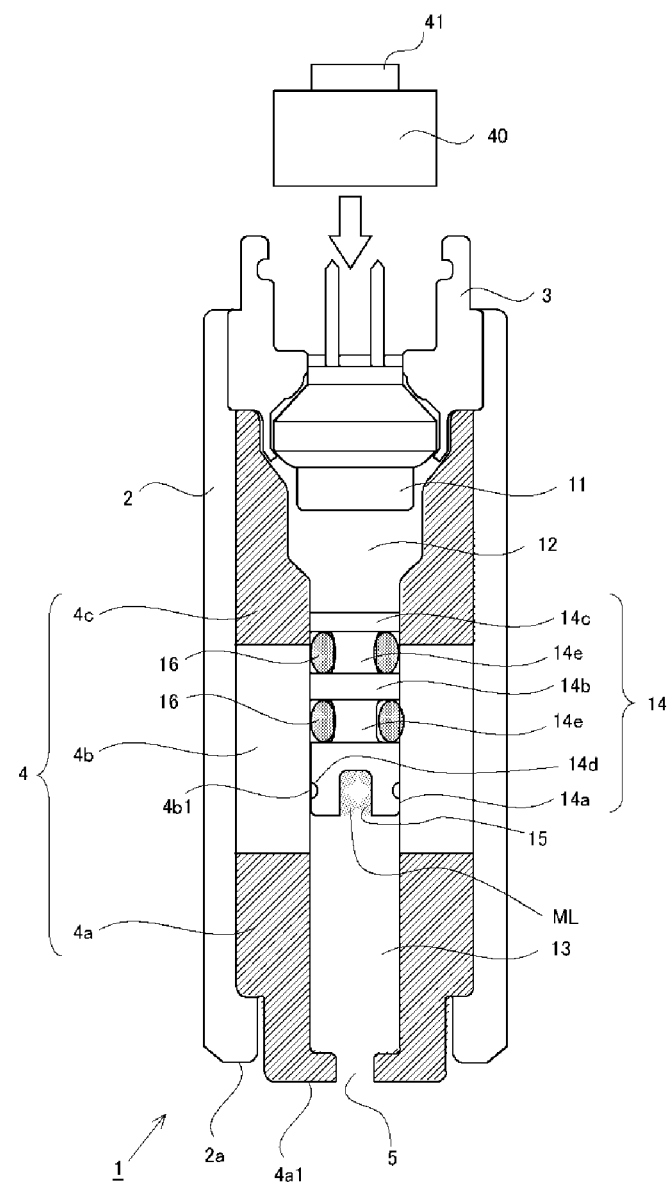
FIG. 1 shows a schematic structure of a needleless syringe according to the present invention.
Figure 2:
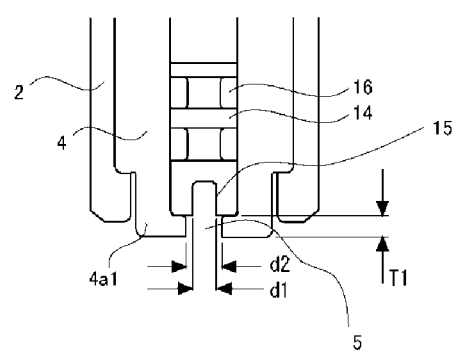
FIG. 2 shows a structure in the vicinity of a front end surface of the needleless syringe according to the present invention.

In this context, FIGS. 1 and 2 show the schematic structure of the syringe 1. FIG. 1 shows a sectional view taken in the longitudinal direction of the syringe 1, and FIG. 2 shows a sectional view illustrating the structure in the vicinity of a front end surface of the syringe 1. The syringe 1 includes, as a main syringe body thereof, a housing having an outer shell container 2 and an inner shell container 4 which is installed at the inside of the outer shell container 2. Note that in the following description of this specification, the injection objective substance, which is to be injected into the injection target area by the syringe 1, is generally referred to as "injection substance". However, this description includes no intention to limit the contents and the form of the substance to be injected. The component, which is to be delivered, for example, to a skin structure, may be either dissolved or not dissolved in the injection substance. Any specified form of the injection substance is available without any problem as well, for which various forms can be adopted, including, for example, liquid, gel form and solid, provided that the injection substance can be discharged to the injection target area by means of the energy obtained from an igniter 11 described later on. Note that in this embodiment, the following explanation will be made assuming that the "injection substance" is the substance based on a powder or a granule. Further, in this specification, the direction (downward direction in the drawing in the example shown in FIG. 1), in which the injection substance is discharged by the syringe 1, is defined as "frontward direction of the syringe 1". Therefore, the upward direction in FIG. 1, which is opposite thereto, is the backward direction of the syringe 1.

In this embodiment, the housing of the syringe 1 is formed by installing the inner shell container 4 into the outer shell container 2 as described above. Then, the inner shell container 4 has a first portion 4a, a second portion 4b, and third portion 4c. The first portion 4a and the third portion 4c are made of metal, and the second portion 4b is made of resin. When the inner shell container 4 is installed into the outer shell container 2, then the first portion 4a, the second portion 4b, and the third portion 4c may be integrated into one unit, and then they may be installed into the outer shell container 2 in this state. In another method, the first portion 4a, the second portion 4b, and the third portion 4c may be successively installed in this order with respect to the outer shell container 2.

In this context, as understood from FIG. 1 as well, the first portion 4a is positioned at a front position at the inside of the outer shell container 2 in a state in which the first portion 4a is caught by a brim portion which is provided at a front position of the outer shell container 2. In this situation, a front end surface 4a1, which is the end surface disposed on the front side of the first portion 4a, is in a state of protruding from a front end surface 2a of the outer shell container 2. Then, an opening 5, which connects the inside of the inner shell container 4 (sliding movement passage 13 described later on) and the outside of the syringe 1, is provided at the front end surface 4a1. As shown in FIG. 2, the opening 5 is formed to have a columnar shape having an inner diameter d2. Note that the inner diameter d2 is smaller than the inner diameter of the sliding movement passage 13. Then, a through-hole, which is connected to the opening 5 and which extends in the axial direction of the syringe 1, is formed at the inside of the first portion 4a. The through-hole forms a part of the sliding movement passage 13 described later on.

In the next place, as shown in FIG. 1, the second portion 4b is arranged so that the second portion 4b is adjacent to the first portion 4a at the inside of the outer shell container 2. The second portion 4b is also formed with a through-hole which extends in the axial direction of the syringe 1 in the same manner as the first portion 4a. The through-hole forms a part of the sliding movement passage 13 as described later on. Further, a projection 4b1, which protrudes by a slight amount on the side of the through-hole, is provided at a predetermined position of the through-hole at the second portion 4b.

In the next place, as shown in FIG. 1, the third portion 4c is arranged so that the third portion 4c is adjacent to the second portion 4b at the inside of the outer shell container 2. The third portion 4c is formed with a through-hole which extends in the axial direction of the syringe 1 in the same manner as the first and second portions 4a, 4b, and a combustion chamber 12 which is connected to the through-hole and which has a cross section formed to be wider than that of the through-hole. The through-hole of the third portion 4c also forms a part of the sliding movement passage 13 described later on. Further, the combustion chamber 12 is the space in which a high temperature and high pressure environment is formed by a combustion product produced by the combustion of an ignition charge in an igniter 11 as described later on. When the inner shell container 4 is installed into the interior of the outer shell container 2 as described above, an igniter holder 3, to which the igniter 11 is installed, is further arranged thereon. When the igniter holder 3 is arranged on the inner shell container 4, the combustion chamber 12 is positioned on the side on which the combustion product produced by the igniter 11 is released as shown in FIG. 1.

Note that the igniter 11 is an electric igniter which has the ignition charge therein and which generates the energy in order to discharge the injection substance by means of the combustion thereof. The ignition charge to be used in the igniter 11 is preferably exemplified by a propellant containing zirconium and potassium perchlorate (ZPP), a propellant containing titanium hydride and potassium perchlorate (THPP), a propellant containing titanium and potassium perchlorate (TiPP), a propellant containing aluminum and potassium perchlorate (APP), a propellant containing aluminum and bismuth oxide (ABO), a propellant containing aluminum and molybdenum oxide (AMO), a propellant containing aluminum and copper oxide (ACO), and a propellant containing aluminum and iron oxide (AFO), or a propellant composed of a combination of a plurality of the foregoing propellants. It is also allowable that any propellant or pyrotechnic charge other than the above is used as the ignition charge, provided that the injection can be performed appropriately.

Note that any additional ignition charge is not especially arranged in the combustion chamber 12 shown in FIG. 1. However, in order to adjust the energy for discharging the injection substance, a gas producing agent or the like, which combusts by the combustion product produced by the combustion of the propellant in the igniter 11 and which produces the gas, can be also arranged in the combustion chamber 12. An example of the gas producing agent is exemplified by a single base smokeless propellant composed of 98% by mass of nitrocellulose, 0.8% by mass of diphenylamine, and 1.2% by mass of potassium sulfate. Further, it is also possible to use a variety of gas producing agents used for a gas generator for an air bag and a gas generator for a seat belt pretensioner. It is possible to change the combustion completion time of the gas producing agent by adjusting the dimension, the size, and/or the shape, especially the surface shape of the gas producing agent when the gas producing agent is arranged in the combustion chamber 12. Accordingly, the pressure transition to be generated can be a desired transition, i.e., a transition with which the injection substance can appropriately arrive at the injection target area. In the present invention, the igniter 11 is provided as the driver. The gas producing agent or the like, which is optionally used, is also included in the driver.

In this context, in the case of the syringe 1, a battery 40, which supplies the electric power to the igniter 11, is detachably attached to the igniter holder 3. In relation thereto, a relatively large amount of the electric power can be stored in the battery 40. On the other hand, as for the igniter 11, when the ignition charge is combusted therein, it is necessary to replace the igniter 11 with a new igniter. Therefore, it is necessary that the igniter 11 should be exchanged every time when the igniter 11 is used. However, the battery 40 can be used repeatedly until the electric power can be supplied. Further, a startup switch 41 is provided in order to operate the electric power supply from the battery 40.

In this context, as shown in FIG. 1, when the inner shell container 4 is installed into the interior of the outer shell container 2, then the through-holes, which are formed in the first portion 4a, the second portion 4b, and the third portion 4c, are connected to one another, and thus the sliding movement passage 13 is formed. The sliding movement passage 13 is the space which extends in the axial direction of the syringe 1 and which is formed to have a columnar shape. The sliding movement passage 13 is formed so that a piston 14 (holding unit) made of metal described later on is slidable. Therefore, the through-holes of the respective portions are provided so that the sliding movement passage 13, in which the piston 14 is slidable, is formed by successively installing the first portion 4a, the second portion 4b, and the third portion 4c into the outer shell container 2. Then, the piston 14 is inserted into the sliding movement passage 13 before the igniter holder 3 is installed after the inner shell container 4 is installed into the outer shell container 2.

The piston 14 has a head portion 14a, a first cylindrical portion 14b, and a second cylindrical portion 14c which make contact with the inner wall surface of the sliding movement passage 13. Then, the head portion 14a, the first cylindrical portion 14b, and the second cylindrical portion 14c are connected by connecting portions 14e having a diameter smaller than the inner diameter of the sliding movement passage 13, and thus the piston 14 is formed. Then, the diameter of the connecting portion 14e is smaller than the inner diameter of the sliding movement passage 13. Therefore, seal members 16 made of resin are provided in spaces formed between the connecting portions 14e and the inner wall surface of the sliding movement passage 13 (respective spaces between the head portion 14a and the first cylindrical portion 14b and between the first cylindrical portion 14b and the second cylindrical portion 14c). The seal members 16 do not inhibit the smooth sliding movement of the piston 14, and the seal members 16 hermetically isolate the two spaces of the sliding movement passage 13 between which the piston 14 is interposed, i.e., the space disposed on the side on which the opening 5 is positioned (space on the front side) and the space disposed on the side on which the igniter 11 is positioned (space on the back side). Specifically, for example, butyl rubber and silicon rubber can be adopted as the material for the seal member 16. Further, there are exemplified styrene-based elastomer and hydrogenated styrene-based elastomer as well as those obtained by mixing therewith polyolefin such as polyethylene, polypropylene, polybutene, α-olefin copolymer and the like, oil and talk such as liquid paraffin, process oil and the like, cast, powder inorganic substance such as mica and the like. Further, it is also possible to adopt, as the material for the seal member 16, polyvinyl chloride-based elastomer, olefin-based elastomer, polyester-based elastomer, polyamide-based elastomer, polyurethane-based elastomer, and various rubber materials (especially those subjected to the vulcanization treatment) such as natural rubber, isoprene rubber, chloroprene rubber, nitrile-butadiene rubber, and styrene-butadiene rubber. Further, it is also possible to adopt, as the material for the seal member 16, as well as mixtures thereof and the like.

Further, a recess 14d is formed on a side surface of the head portion 14a of the piston 14 (contact surface with respect to the inner wall surface of the sliding movement passage 13). The recess 14d has a shape to which the projection 4b1 provided for the second portion 4b of the inner shell container 4 is fitted. In this case, as described above, the second portion 4b and the projection 4b1 are formed of resin. Therefore, when the piston 14 is inserted into the sliding movement passage 13 from the back of the sliding movement passage 13, the projection 4b1 is fitted into the recess 14d of the head portion 14a while causing the deformation. Accordingly, the initial position of the piston 14 is determined in the syringe 1. As shown in an upper part (a) of FIG. 3 described later on, the initial position is the position of the piston 14 at which the distance between the skin and the forward end of the piston 14 is a predetermined distance ΔL1 in a state in which the syringe 1 is allowed to abut against the skin as the injection target area.

Then, when the energy is applied from the igniter 11 to the piston 14 which is placed at the initial position, then the fitting between the projection 4b1 and the recess 14d is released, and the piston 14 makes the sliding movement. The resin materials of the second portion 4b and the projection 4b1 are selected so that the fitting to position the piston 14 and the release from the fitting upon the application of the energy are appropriately performed as described above. For example, as for the resin material, it is possible to use, for example, known nylon 6-12, polyarylate, polybutylene terephthalate, polyphenylene sulfide, or liquid crystal polymer. Further, it is also allowable that the resin as described above contains a filling material such as glass fiber, glass filler and the like. Polybutylene terephthalate may contain 20 to 80% by mass of glass fiber, polyphenylene sulfide may contain 20 to 80% by mass of glass fiber, and liquid crystal polymer may contain 20 to 80% by mass of mineral.

In this case, the piston 14 is inserted into the sliding movement passage 13 so that the second cylindrical portion 14c is positioned on the side on which the combustion product produced by the combustion of the ignition charge in the igniter 11 is released, and the piston 14 is positioned at the initial position. In this state, an accommodating recess 15 (accommodating unit), which releasably accommodates the injection substance ML, is formed to have a columnar shape at the front end surface of the head portion 14a of the piston 14. Specifically, the injection substance ML is pressed against and installed into the accommodating recess 15 at a predetermined pressure, and thus an accommodating state, in which the injection substance ML is releasable, is formed. Then, the accommodating recess 15 is provided at the head portion 14a disposed on the side opposite to the second cylindrical portion 14c exposed to the combustion product. Therefore, it is possible to suppress the injection substance ML from being exposed to the combustion product, by means of the seal members 16 arranged for the piston 14. Note that the inner diameter of the accommodating recess 15 is d1 as shown in FIG. 2, and the inner diameter of the accommodating recess 15 is smaller than the inner diameter d2 of the opening 5.

An explanation will now be made on the basis of FIG. 2 about the correlation between the accommodating recess 15 and the opening 5. FIG. 2 shows a state in which the head portion 14a of the piston 14 abuts against the inner wall surface of the front end surface 4a1. The position of the piston 14 in the sliding movement passage 13 in this state is referred to as "abutment position". In this context, as described above, the inner diameter d1 of the accommodating recess 15 is smaller than the inner diameter d2 of the opening 5. Therefore, when the piston 14 is disposed at the abutment position, then the accommodating recess 15 and the opening 5 are in an adjoining state, and they overlapped so that the end surface area of the accommodating recess 15 is included in the opening area of the opening 5. Further, when the piston 14 is disposed at the abutment position, a space, which is separated by a thickness T1 of the front end surface 4a1, is formed between the end surface of the accommodating recess 15 and the outer surface of the front end surface 4a1 which is brought in contact with the injection target area such as the skin or the like.

<Operation of Syringe 1>

Figure 3:
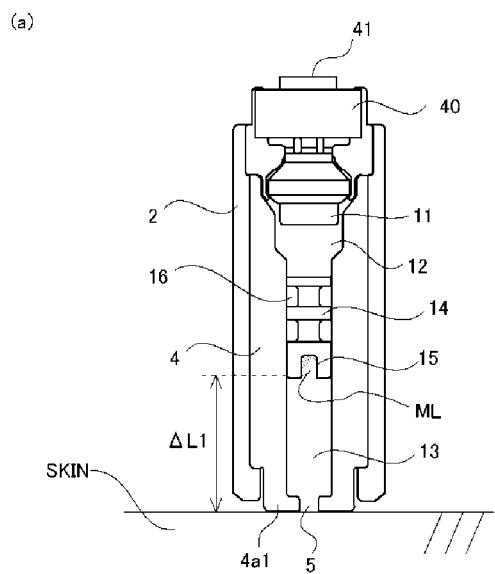
FIG. 3 explains the operation of the needleless syringe according to the present invention.
Figure 3:
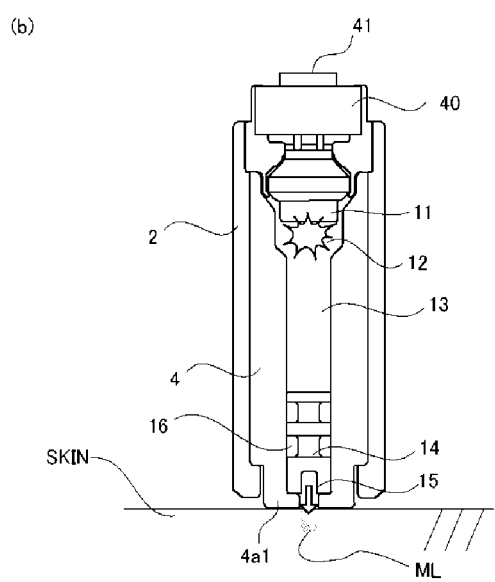

An explanation will be made on the basis of FIG. 3 about the discharge of the injection substance ML by the syringe 1 constructed as described above. The upper part (a) of FIG. 3 shows a state in which the piston 14 is disposed at the initial position, wherein the front end surface of the syringe 1, i.e., the front end surface 4a1 on which the opening 5 is provided is brought in contact with the skin which is the injection target area. In this state, the distance between the skin surface and the front end surface of the piston 14 is secured by ΔL1. Therefore, the piston 14 is in such a state that the piston 14 is slidable by a distance (ΔL1−T1) obtained by subtracting the thickness T1 of the front end surface 4a1 from the distance ΔL1 at the inside of the sliding movement passage 13 before the use of the syringe 1 (before the discharge of the injection substance ML).

Then, when the startup switch 41 is depressed by a user in the state shown in FIG. 3(a), then the electric power is thereby supplied from the battery 40 to the igniter 11, and the ignition charge is combusted in the igniter 11. As a result, the combustion product is released into the combustion chamber 12, the piston 14 is pressurized, and thus the piston 14 progressively slides in the sliding movement passage 13. In the sliding movement process, the combustion product is suppressed from making a detour to arrive at the front portion of the piston 14, owing to the hermetic sealing performance of the seal members 16 arranged in the piston 14. The injection substance ML, which is accommodated in the accommodating recess 15, is prevented from being brought in contact with the combustion product.

Then, the piston 14 progressively slides in the sliding movement passage in accordance with the pressurization. Finally, as shown in a lower part (b) of FIG. 3, the head portion 14a of the piston 14 collides with the inner wall surface of the front end surface 4a1, and the movement of the piston 14 is suddenly stopped. Note that in this situation, the piston 14 arrives at the abutment position shown in FIG. 2. As a result, the momentum, which has been possessed by the piston 14 until just before the collision, is transferred to the injection substance ML which has been accommodated in the accommodating recess 15. The injection substance ML is released frontwardly simultaneously with the collision. In this situation, the mass of the injection substance ML is relatively smaller than the mass of the piston 14. Therefore, in accordance with the theorem of conservation of momentum, the release speed of the injection substance ML after the collision is increased as compared with the speed of the piston 14 having been provided until that time. As a result, the released injection substance ML flies toward the skin in a state in which the injection substance ML has a speed sufficient to penetrate through the surface of the skin as the injection target area.

Further, when the injection substance ML is released as described above, the injection substance ML is never exposed to the combustion gas containing the combustion product which is the medium for carrying the energy applied from the igniter 11. Therefore, it is possible to effectively suppress the formation of fine particles of the injection substance ML during the release of the injection substance ML unlike the conventional technique. Further, the injection substance ML arrives at the skin without being exposed to the combustion gas. Therefore, it is possible to reliably suppress the invasion of the combustion gas into the skin.

Further, as shown in FIG. 2, the end surface area of the accommodating recess 15 is overlapped so that the end surface area of the accommodating recess 15 is included in the opening area of the opening 5. Therefore, the injection substance ML, which is released frontwardly in accordance with the collision between the piston 14 and the front end surface 4a1, can be maximally prevented from being brought in contact with the inner wall surface of the opening 5 and being adhered thereto. Thus, it is possible to realize the efficient injection of the injection substance ML. Further, owing to the presence of the opening 5, the flying space which is provided to allow the injection substance ML to fly toward the skin, i.e., the flying space which has a diameter of d2 and a height of T1 is formed between the accommodating recess 15 and the skin. Owing to the presence of the flying space, the momentum, which is possessed by the piston 14, can be effectively transferred to the injection substance ML. It is possible to realize the preferred discharge of the injection substance ML.

Note that based on a physical viewpoint, in order to raise the release speed of the injection substance ML in accordance with the collision described above, when the piston 14, which slides along the sliding movement passage 13, is stopped by the collision, it is preferable that the deformation of the front end surface 4a1 is suppressed as far as possible upon the collision, and the backward rebounding of the piston 14, which is caused by the collision, is suppressed as far as possible. Accordingly, in view of the matters as described above, it is preferable to adjust, for example, the strength and the shape of the front end surface 4a1 and the coefficient of rebound between the piston 14 and the front end surface 4a1.

Further, in the syringe 1, the piston 14 can be always placed at the same initial position in accordance with the fitting relationship between the projection 4b1 and the recess 14d. Therefore, it is possible to maintain the approximately constant momentum which is to be transferred to the injection substance ML in accordance with the collision between the piston 14 and the front end surface 4a1. This fact contributes to the stabilization of the injection performance of the syringe 1. In view of the above, according to the syringe 1 concerning the present invention, it is possible to realize the efficient injection of the injection substance ML, and thus it is possible to exhibit the high injection performance of the syringe 1.

First Modified Embodiment

In the case of the structure shown in FIG. 1, one accommodating recess 15 for accommodating the injection substance ML is formed at the head portion 14a of the piston 14. However, in this modified embodiment, in place of this mode, it is also allowable to provide a plurality of accommodating recesses 15 at the head portion 14a. In this case, it is preferable that all of end surface areas of the plurality of accommodating recesses 15 are overlapped to be included in the opening area of the opening 5 when the piston 14 is disposed at the abutment position to collide with the front end surface 4a1.

Second Modified Embodiment

Figure 4:
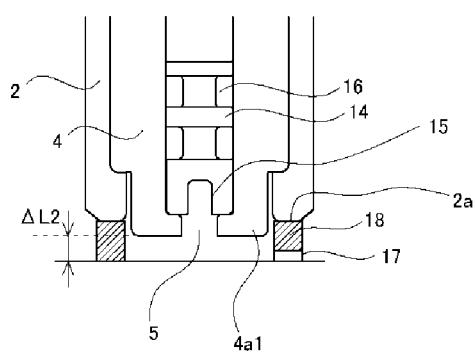
FIG. 4 shows another structure in the vicinity of the front end surface of the needleless syringe according to the present invention.
Figure 5:
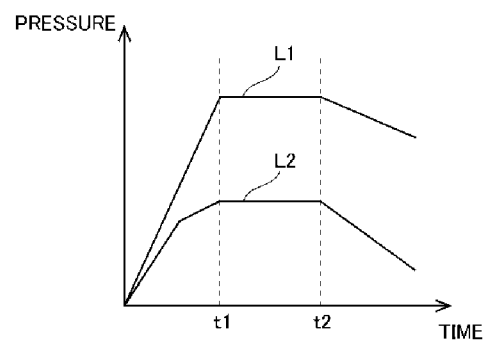
FIG. 5 shows the pressure transition at the inside of a spacer of the needleless syringe shown in FIG. 4.

This modified embodiment will be explained on the basis of FIGS. 4 and 5. FIG. 4 shows a state in which the head portion 14a of the piston 14 abuts against the inner wall surface of the front end surface 4a1 in the syringe 1 according to this modified embodiment. In this modified embodiment, an annular spacer 18 is arranged to surround the opening 5 on the front end surface 2a of the outer shell container 2. Note that the outer shell container 2, the inner shell container 4, the opening 5, and the piston 14 are constructed in the same manner as in the embodiment described above. Then, the front end surface of the spacer 18 is positioned frontwardly as compared with the front end surface 4a1 of the first portion 4a which is provided with the opening 5. Therefore, when the syringe 1 is brought in contact with the injection target area in order to inject the injection substance ML, as shown in FIG. 4, such a state is given that the front end surface 4a1 is not brought in contact with the injection target area, and only the front end surface of the spacer 18 is brought in contact therewith. Note that the distance between the front end surface 4a1 and the surface of the injection target area is ΔL2. When the flying space described above is formed between the opening 5 and the injection target area by means of the spacer 18 as described above, it is thereby possible to realize the effective injection of the injection substance ML.

In this case, when the piston 14 slides along the sliding movement passage 13 toward the opening 5, then the air, which has been contained in the sliding movement passage 13, is discharged from the opening 5, and the air flows into the internal space of the spacer 18 (space on which the opening 5 is open to discharge the injection substance ML). Therefore, the pressure of the internal space is raised. As a result, the released injection substance ML may be inhibited from arriving at the injection target area in some cases, and/or it may become difficult to stably press and hold the spacer 18 against the injection target area due to the increase in pressure in other cases. Accordingly, the spacer 18 is provided with a plurality of communication passages 17 which make communication between the internal space of the spacer 18 and the external space of the syringe 1.

When the communication passages 17 are provided as described above, it is possible to suppress the increase in pressure in the internal space of the spacer 18 caused by the sliding movement of the piston 14. In this context, FIG. 5 shows the pressure transition (transition indicated by a line L1) of the internal space of the spacer 18 provided when the communication passages 17 are not provided for the spacer 18, and the pressure transition (transition indicated by a line L2) of the internal space of the spacer 18 according to this modified embodiment. The time t1 shown in FIG. 5 is the time at which the piston 14 arrives at the abutment position, and the time t2 is the time at which the released injection substance ML arrives at the injection target area. It is possible to understand that the increase in pressure in the internal space of the spacer 18 is effectively suppressed owing to the presence of the communication passages 17 as described above. Note that, FIG. 5 shows the concept of the pressure change, which does not show any absolute numerical value and any absolute change.

Second Embodiment

Figure 6:
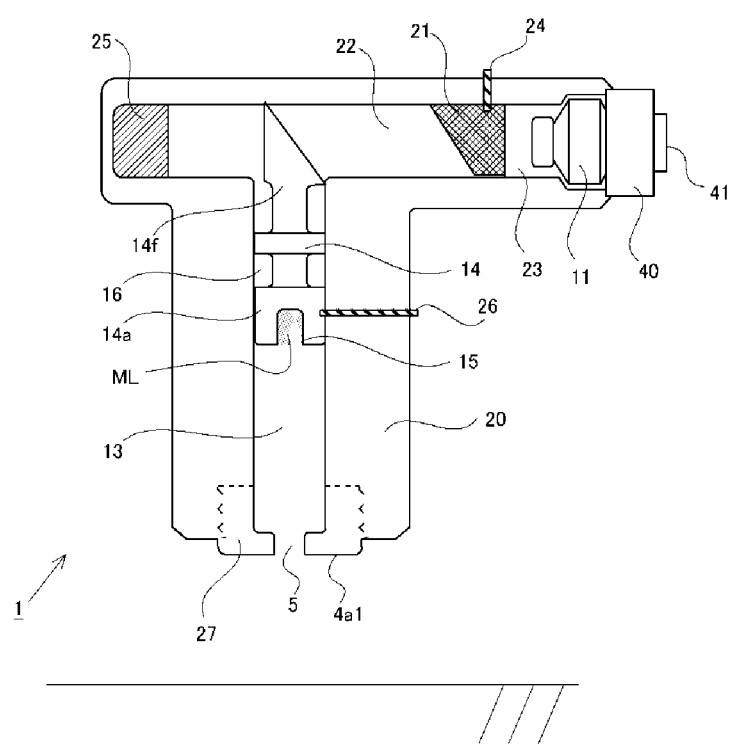
FIG. 6 shows a second drawing illustrating a schematic structure of a needleless syringe according to the present invention.

Next, a second embodiment of the syringe 1 according to the present invention will be explained on the basis of FIG. 6. Note that those included in the components of a syringe 1 shown in FIG. 6, which are the same as the components of the syringe 1 referred to in the first embodiment described above (including those which are substantially the same), are designated by the same reference numerals, any detailed explanation of which will be omitted. A housing 20, which is the main syringe body of the syringe 1 according to this embodiment, is formed with a rod movement passage 22 in which a rod 21 is movable, in addition to the sliding movement passage 13 which is formed so that the piston 14 slides. Then, the rod movement passage 22 is connected to the sliding movement passage 13. As shown in FIG. 6, a T-shaped passage is formed by the both passages.

The rod 21 is formed so that an end surface, which faces or confronts the igniter 11, is generally perpendicular to the length direction of the rod movement passage 22, and the pressure, which is generated by the combustion of the ignition charge in the igniter 11, is efficiently received with ease (the end surface is referred to as "vertical end surface"). On the other hand, the other end surface of the rod 21 (end surface disposed on the side opposite to the end surface opposed to the igniter 11) is an inclined surface which is inclined by 45 degrees with respect to the length direction of the rod movement passage 22 as shown in FIG. 6 (the end surface is referred to as "inclined end surface"). Note that, a combustion chamber 23 is formed between the igniter 11 and the vertical end surface of the rod 21. Further, a cushion 25, which is formed of a buffering material, is arranged at an end portion of the rod movement passage 22 disposed on the side opposite to the end portion at which the igniter 11 is arranged.

In the rod movement passage 22, the initial position of the rod 21 is determined by a shear pin 24 made of resin. The shear pin 24 penetrates through the housing 20 disposed around the rod movement passage 22, and the shear pin 24 is inserted into a positioning hole provided on the rod 21. Accordingly, the shear pin 24 defines the initial position of the rod 21 with respect to the housing 20. The initial position of the piston 14 in the sliding movement passage 13 is determined so that an inclined end surface of a tail portion 14f of the piston 14 (portion disposed on the side opposite to the head portion 14a) is opposed to the inclined end surface of the rod 21 positioned at the initial position (in a state in which the tail portion 14f protrudes to the rod movement passage 22). In this situation, the piston 14 is fixed by means of a shear pin 26 made of resin. The shear pin 26 penetrates through the housing 20 disposed around the sliding movement passage 13, and the shear pin 26 is inserted into a positioning hole provided on the piston 14. Accordingly, the shear pin 26 defines the initial position of the piston 14 with respect to the housing 20.

Note that the sliding movement passage 13 and the rod movement passage 22 are formed in the housing 20 as described above. Therefore, it is necessary that the piston 14 should be inserted into the inside from the end portion of the sliding movement passage 13 disposed on the side on which the opening 5 is provided. In view of the above, in order that the piston 14 can be inserted into the sliding movement passage 13, a front member 27, which forms the opening 5 and the front end surface 4a1 for allowing the piston 14 to collide therewith upon the discharge of the injection substance ML and which is composed of a member distinct from the housing 20, is attached to the front end portion of the sliding movement passage 13 so that the front member 27 is detachable with respect to the housing 20. In this embodiment, the front member 27 is screw-engaged with the housing 20. Note that the rod 21 is inserted into the inside from the end portion at which the igniter 11 is arranged, of the end portions of the rod movement passage 22. The rod 21 is fixed by the shear pin 24 at the initial position.

When the energy is applied to the rod 21 by the combustion of the ignition charge in the igniter 11 constructed as described above, then the shear pin 24 is broken, and the rod 21 moves in the rod movement passage 22 toward the tail portion 14f of the piston 14. Then, when the inclined end surface of the rod 21 is brought in contact with the inclined end surface of the tail portion 14f of the piston 14, then most of the momentum possessed by the rod 21 is transferred to the piston 14, and the shear pin 26 is broken. Accordingly, the piston 14 starts the sliding movement in the sliding movement passage 13. As a result, the piston 14 collides with the front end surface 4a1, and the injection substance ML is discharged to the injection target area via the opening 5. Note that any large amount of the momentum does not remain in the rod 21 as a result of the contact of the rod 21 with the piston 14. However, if the movement of the rod 21 in the rod movement passage 22 continues on account of the remaining momentum, the rod 21 is stopped by the cushion 25.

As described above, also in the case of the syringe 1 according to this embodiment, it is possible to realize the efficient injection of the injection substance ML, and thus it is possible to exhibit the high injection performance of the syringe 1, in the same manner as in the first embodiment described above. Further, the direction, in which the energy is applied from the igniter 11 to the piston 14 disposed in the sliding movement passage 13, can be freely set by adopting the structure in which the energy coming from the igniter 11 is transmitted to the piston 14 by the aid of the rod 21. Therefore, it is possible to freely adjust the relative position between the sliding movement passage 13 and the igniter 11 in the housing 20. Thus, the degree of freedom of the design of the syringe 1 is raised. It is also possible to realize the compact syringe 1 in some cases.

OTHER EMBODIMENTS

According to the syringe 1 concerning the present invention, for example, cultured cells or stem cells can be seeded or inoculated with respect to cells or scaffold tissue (scaffold) as the injection target in the field of the regenerative medicine for human, other than the case in which the injection substance is injected into the skin structure as described above. For example, as described in JP2008-206477A, it is possible to inject, by the syringe 1, cells which may be appropriately determined by those skilled in the art depending on the portion subjected to the transplantation and the purpose of the cell regeneration, for example, endothelial cell, endothelial precursor cell, myeloid cell, preosteoblast, chondrocyte, fibroblast, skin cell, muscle cell, liver cell, kidney cell, intestinal tract cell, and stem cell, as well as every cell considered in the field of the regenerative medicine.

Further, the syringe 1 according to the present invention can be also used to deliver DNA or the like, for example, to cells or scaffold tissue (scaffold) as described in JP2007-525192W. In this case, it is possible to suppress the influence exerted, for example, on cells themselves or scaffold tissue (scaffold) itself when the syringe 1 according to the present invention is used, as compared with when the delivery is performed by using any needle. Therefore, it is affirmed that the use of the syringe 1 according to the present invention is more preferred.

Further, the syringe 1 according to the present invention is also preferably used, for example, when various genes, cancer suppressing cells, or lipid envelops are directly delivered to the objective tissue and when the antigen gene is administered in order to enhance the immunity against the pathogen. Other than the above, the syringe 1 can be also used, for example, for the field of the medical treatment for various diseases (field as described, for example, in JP2008-508881W and JP2010-503616W) and the field of the immunological medical treatment (immunotherapy) (field as described, for example, in JP2005-523679W). The field, in which the syringe 1 is usable, is not intentionally limited. For example, when the injection target is an animal, for example, a biodegradable resin incorporated with an IC chip can be injected by using the syringe of the present invention.

The invention claimed is:
1. A needleless syringe for injecting an injection objective substance into an injection target area of a living body without using any injection needle, the needleless syringe comprising:
a main syringe body which is a main body of the needleless syringe and which has, in the main body, a sliding movement passage connected to an opening provided on a front end surface of the main body, the main syringe body having an inner wall, at least one projection formed on the inner wall;
a holding unit which is arranged slidably in the sliding movement passage and which has an accommodating unit for accommodating the injection objective substance so that the injection objective substance is releasable, the holding unit having an outer surface facing the inner wall of the main syringe body, at least one recess formed on the outer surface; and
a driver that is configured to apply energy to the holding unit fixed to the main syringe body and arranged at an initial position separated by a predetermined distance from the opening in the sliding movement passage in order to allow the holding unit to slide toward the opening, the at least one projection at least partially disposed in the at least one recess at the initial position and configured to be removed from the at least one recess in response to the energy being applied to the holding unit, wherein the outer surface of the holding unit is configured to be deformed when the at least one projection is disposed in the at least one recess, and wherein:
the opening is arranged so that the opening adjoins the accommodating unit when the holding unit is at an abutment position at which the holding unit abuts against the opening and sliding movement thereof is inhibited in the sliding movement passage;
the accommodating unit is formed at a first end surface of the holding unit facing the opening so that the accommodating unit does not penetrate in an axial direction of the holding unit; and
when the energy is applied by the driver to the holding unit disposed at the initial position, then the holding unit is released from the main syringe body and starts to slide in the sliding movement passage to abut against the opening at the abutment position, and thus the injection objective substance accommodated in the accommodating unit is discharged via the opening.
2. The needleless syringe according to claim 1, wherein a space on a driver side on which the driver is arranged and a space on an opening side which is connected to the opening are hermetically isolated from each other by the holding unit in the sliding movement passage.
3. The needleless syringe according to claim 2, wherein:
the driver is an ignition device in which a propellant is combusted by supplying an electric power from outside; and
the accommodating unit is arranged at the first end surface disposed on a side opposite to a second end surface of the holding unit with which a combustion product of the propellant is brought in contact.
4. The needleless syringe according to claim 1, wherein the accommodating unit is arranged at a plurality of positions on the first end surface of the holding unit disposed on a side of the opening when the holding unit is disposed at the abutment position in the sliding movement passage.
5. The needleless syringe according to claim 1, wherein:
an inner diameter of the opening is smaller than an inner diameter of the sliding movement passage; and an end surface area of the accommodating unit disposed on a side of the opening is overlapped so that the end surface area is included in an opening area of the opening when the holding unit is disposed at the abutment position.

6. The needleless syringe according to claim 5, wherein the main syringe body has a predetermined thickness in a discharge direction of the injection objective substance at the front end surface at which the opening is provided, and thus a flying space, in which the injection objective substance flies, is formed in the opening.

7. The needleless syringe according to claim 1, further comprising:
a spacer which is formed to surround the opening at outside of the front end surface of the main syringe body and which protrudes frontwardly from the main syringe body, wherein:
a communication passage, which makes communication between an internal space of the spacer and an external space of the spacer in a state of abutment of the spacer against the injection target area, is provided for the spacer.

8. The needleless syringe according to claim 1, further comprising:
a rod to which the energy applied from the driver is applied prior to the holding unit; and
a rod movement passage which is provided in nonparallel to the sliding movement passage in the main syringe body and which allows the rod to move therein, wherein:
the holding unit is arranged at the initial position so that a tail portion, which is disposed on a side opposite in the axial direction to a side of formation of the accommodating unit, protrudes into the rod movement passage; and
when the energy is applied to the rod by the driver, then the rod moves in the rod movement passage, the rod is brought in contact with the holding unit disposed at the initial position, and thus the sliding movement of the holding unit is started in the sliding movement passage.

9. The needleless syringe according to claim 1, wherein the holding unit is disposed on the inner wall of the main syringe body at the initial position.

10. The needleless syringe according to claim 1, wherein the holding unit is in direct physical contact with the inner wall of the main syringe body at the initial position.

11. The needleless syringe according to claim 1, further comprising at least one seal member arranged in the holding unit and configured to suppress the injection objective substance from being exposed to a combustion product generated by the driver in a combustion chamber disposed between the holding unit and the driver.

12. The needleless syringe according to claim 11, wherein the at least one seal member directly contacts the inner wall of the main syringe body at the initial position.

13. The needleless syringe according to claim 11, wherein at least a portion of the combustion chamber is wider than the sliding movement passage.

14. A needleless syringe for injecting an injection objective substance into an injection target area of a living body without using any injection needle, the needleless syringe comprising:
a main syringe body which is a main body of the needleless syringe and which has, in the main body, a sliding movement passage connected to an opening provided on a front end surface of the main body, the main syringe body having an inner wall, at least one projection formed on the inner wall;
a holding unit arranged slidably in the sliding movement passage, the holding unit comprising an accommodating unit configured to accommodate the injection objective substance so that the injection objective substance is releasable, the holding unit having an outer surface facing the inner wall of the main syringe body, at least one recess formed on the outer surface; and
a driver configured to apply energy to the holding unit arranged at an initial position separated by a predetermined distance from the opening in the sliding movement passage in order to allow the holding unit to slide toward the opening, the outer surface of the holding unit directly contacting the inner wall of the main syringe body at the initial position, the at least one projection at least partially disposed in the at least one recess at the initial position and configured to be removed from the at least one recess in response to the energy being applied to the holding unit, wherein the outer surface of the holding unit is configured to be deformed when the at least one projection is disposed in the at least one recess, and
wherein the holding unit is configured to be released from the main syringe body and start to slide in the sliding movement passage to abut against the opening at an abutment position at which the holding unit abuts against the opening such that the injection objective substance accommodated in the accommodating unit is discharged via the opening, when the energy is applied by the driver to the holding unit disposed at the initial position.

15. The needleless syringe according to claim 14, wherein the holding unit is fixed to the inner wall of the main syringe body at the initial position.

16. A needleless syringe for injecting an injection substance into an injection target area of a living body without using any injection needle, the needleless syringe comprising:
a housing having a sliding movement passage and a rod movement passage arranged so as to cross the sliding movement passage, the sliding movement passage having an inner wall and an opening on a front end surface of the housing;
a holding unit having an outer surface and being disposed in the sliding movement passage so as to be slidable from an initial position towards the opening, the outer surface directly contacting the inner wall of the housing when the holding unit is in the initial position, the initial position being a predetermined distance from the opening;
a rod disposed in the rod movement passage so as to be movable in a direction towards at least a portion of the holding unit;
a driver configured to apply energy that causes the rod to slide along the sliding movement passage and contact the holding unit when the holding unit is in the initial position, the contact causing the holding unit to slide toward the opening;
a shear pin supporting the rod and configured to break in response to the energy being applied to the rod; and
an accommodating unit supported by the holding unit and configured to hold the injection substance until the injection substance is released.

17. The needleless syringe according to claim 16, wherein the shear pin extends from the rod and into at least a portion of a wall of the housing.

18. The needleless syringe according to claim 16, wherein the portion of the holding unit is a tail portion.

19. The needleless syringe according to claim 16, wherein the direction is substantially perpendicular to the sliding movement passage.

* * * * *